(12) United States Patent
Tamura et al.

(10) Patent No.: US 6,306,577 B1
(45) Date of Patent: Oct. 23, 2001

(54) METHOD FOR MEASURING ENZYME REACTION

(75) Inventors: Hiroshi Tamura, Musashimurayama; Shigenori Tanaka, Kodaira, both of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/290,091

(22) Filed: Apr. 12, 1999

(30) Foreign Application Priority Data

Apr. 10, 1998 (JP) .................................................. 10-099665

(51) Int. Cl.$^7$ .............................. C12Q 1/00; G01N 33/53
(52) U.S. Cl. .................................................. 435/4; 435/963
(58) Field of Search .................................. 435/4, 7.1, 7.2, 435/7.21, 7.9, 7.91, 963

(56) References Cited

U.S. PATENT DOCUMENTS

| 4,720,787 | 1/1988 | Lipscomb | 364/416 |
| 5,840,510 | * 11/1998 | Tanaka et al. | 435/23 |
| 5,876,955 | * 3/1999 | Tamura et al. | 435/23 |

FOREIGN PATENT DOCUMENTS

| 0 031 051 A1 | 7/1981 | (EP) . |
| 0 180 905 A2 | 5/1986 | (EP) . |
| 0 426 395 A1 | 5/1991 | (EP) . |
| 0 709 981 A1 | 5/1996 | (EP) . |

OTHER PUBLICATIONS

Dawson, "Endotoxin Standards and CSE Potency", LAL Update, vol. 11, No. 3, pp. 2–5, 1993.*
Joachim Siedel, et al., Determination of Metabolite Concentrations by Kinetic Methods, pp. 182–197, 1983.

* cited by examiner

Primary Examiner—Deborah K. Ware
(74) Attorney, Agent, or Firm—Knobbe, Martens, Olson & Bear LLP

(57) ABSTRACT

A method for measuring an enzyme reaction to determine an amount of a substance involved in the enzyme reaction, which comprises measuring a time course of a parameter of the enzyme reaction, measuring a time required for the parameter of the enzyme reaction to change from a first threshold value to a second threshold value, and correlating the measured time to an amount of the substance involved in the enzyme reaction.

6 Claims, No Drawings

METHOD FOR MEASURING ENZYME REACTION

BACKGROUND OF THE INVENTION

The present invention relates to a method for measuring an enzyme reaction and, more particularly, to a novel method for measuring the Limulus reaction or the phenol oxidase precursor cascade reaction.

It is highly necessary, especially in the medical field, to measure the enzyme reaction whose parameter changes with time. However, it is difficult to accurately measure the reaction unless the rate of change of the parameter of the enzyme reaction is constant.

For example, many infectious diseases are known in the medical field. The greatest care is given to prevent the infectious diseases because there are many cases in which patients become serious due to decrease in immunological competence. It is known that the diagnosis of the infectious diseases is possible by determining substances involved in the enzyme reaction such as endotoxin, $(1\rightarrow3)$-$\beta$-D-glucan, and peptidoglycan which are derived from causative bacteria.

The determination of the amount of endotoxin has conventionally been accomplished by the biological test called rabbit pyrogen test. This test involves problems of individual differences and cost, and presents difficulties in carrying out a large number of tests. Therefore, an endotoxin test using the Limulus reaction is widely used as an alternative test which is a simple and economical test.

The determination using the Limulus reaction is based on the fact that endotoxin or $(1\rightarrow3)$-$\beta$-D-glucan sequentially activates factors in a Limulus amebocyte lysate and causes eventual gelation or hydrolysis of a synthetic peptide substrate. The Limulus reaction is characteristic in that its reaction rate in the presence of endotoxin or $(1\rightarrow3)$-$\beta$-D-glucan gradually increases after a certain period of lag time and then gradually decreases after the stage of reaction at a constant rate (zeroth-order reaction), giving an S-shaped reaction curve. This necessitates careful consideration in the accurate determination of the amount of endotoxin or $(1\rightarrow3)$-$\beta$-D-glucan based on the Limulus reaction. Several methods have been proposed so far.

Among the methods using the Limulus reaction to determine the amount of endotoxin or $(1\rightarrow3)$-$\beta$-D-glucan there is, for example, a kinetic assay (such as calorimetric reaction time assay, turbidimetric reaction time assay, calorimetric reaction rate assay, and turbidimetric reaction rate assay). The calorimetric reaction time assay and the tubidimetric reaction time assay are designed to measure absorbance and turbidity, respectively, and associating a time required for the absorbance or turbidity to reach a prescribed value after the start of reaction with an extent to which the enzyme reaction has proceeded, thereby measuring the Limulus reaction. From the thus obtained value is calculated the amount of endotoxin or $(1\rightarrow3)$-$\beta$-D-glucan. The calorimetric reaction rate assay and the turbidimetric reaction rate assay are designed to obtain a rate at which the absorbance or turbidity changes per unit time in the Limulus reaction that takes place in a prescribed period of time and associate the change rate with an extent to which the enzyme reaction has proceeded, thereby calculating the content of endotoxin or $(1\rightarrow3)$-$\beta$-D-glucan.

In the past, the colorimetric and turbidimetric reaction assays have been the major kinetic methods for determining the amount of endotoxin or $(1\rightarrow3)$-$\beta$-D-glucan. However, there is a case where it takes a certain length of time (lag time) for the Limulus amebocyte lysate to become activated after contact with endotoxin or $(1\rightarrow3)$-$\beta$-D-glucan, with the lag time varying depending on the concentration of endotoxin or $(1\rightarrow3)$-$\beta$-D-glucan, the method of their preparation, and the origins (strains) from which they were derived. There was an instance where even those samples containing endotoxin or $(1\rightarrow3)$-$\beta$-D-glucan in the same amount gave greatly different values depending on the derivation and the method of preparation, from one method to another. The discrepancy in measured values among the methods employed sometimes causes serious problems (such as endotoxin shock), endangering patients, for example, when the amount of endotoxin on medical instruments or in dialysate is underestimated (because of inability to detect the endotoxin contamination exceeding the tolerance, which gives the false-negative reaction).

The reaction rate assay which has been conventionally regarded as most reliable among the methods of endotoxin determination that employ the Limulus reaction, is superior in sensitivity and capability of quantitative determination. On the other hand, it is limited in the range of determination and needs complex steps (such as dilution in the case of some samples). Therefore, it is not necessarily practical.

Peptidoglycan is a substance like endotoxin and $(1\rightarrow3)$-$\beta$-D-glucan, which has a biological activity undesirable for living bodies. It has a variety of biological activities to living bodies, such as pyrexic activity, lowering of liver or renal function, enhancement of endotoxin activity, and adjuvant activity to heighten the immunological function. Consequently, it should be removed from living bodies, drugs, and medical instruments as in the case of endotoxin and $(1\rightarrow3)$-$\beta$-D-glucan.

In the meantime, it is known that the body fluid of insects contains a cascade system which is formed of a series of enzymes called phenol oxidase precursor cascade which is involved in the melanization of the body fluid. The above-mentioned $(1\rightarrow3)$-$\beta$-D-glucan and peptidoglycan trigger this cascade system to eventually form melanin through the cascade reaction (Onishi, Annot. Zool. Jpn., 27, 33–39 (1954); Ashida and Onishi, Arch. Biochem. Biophys., 122, 411–416 (1967); Brunet, Insect Biochem., 10, 467–500 (1980); Ashida and Yamazaki, Molting and Metamorphosis, 239–265, Japan Sci. Press (1990); Ashida and Dohke, Insect Biochem., 10, 37–47 (1980)). A reagent to determine the total amount of $(1\rightarrow3)$-$\beta$-D-glucan and peptidoglycan utilizing this cascade is commercially available under the trade name of "SLP Reagent" from Wako Pure Chemical Industries, Ltd. Measurement using the reagent is the reaction time assay similar to that used to measure the Limulus reaction. Unfortunately, the phenol oxidase precursor cascade reaction also gives the S-shaped reaction curve as in the case of the Limulus reaction and hence it presents difficulties in accurate determination as in the case of determination of endotoxin and $(1\rightarrow3)$-$\beta$-D-glucan by the Limulus reaction.

For the reasons mentioned above, there is a demand for the development of a method for measuring an amount of endotoxin, $(1\rightarrow3)$-$\beta$-D-glucan, or peptidoglycan by the Limulus reaction or the phenol oxidase precursor cascade reaction, which accurately reflects the content of endotoxin, $(1\rightarrow3)$-$\beta$-D-glucan, or peptidoglycan and can be rapidly carried out. Thus, it is an object of the present invention to provide such a method.

SUMMARY OF THE INVENTION

In view of the above-mentioned problems, the present inventors have carried out intensive researches and have found that the problems are solved by using as an index, a time required for a parameter of an enzyme reaction to change within a specific range in an initial stage of the enzyme reaction. The present invention has been achieved based on the findings.

Thus the present invention provides a method for measuring an enzyme reaction to determine an amount of a substance involved in the enzyme reaction, which comprises measuring a time course of a parameter of the enzyme reaction, measuring a time required for the parameter of the enzyme reaction to change from a first threshold value to a second threshold value; and correlating the measured time to an amount of the substance involved in the enzyme reaction (This method is sometime referred to as the assay of the present invention hereinafter.).

In the assay of the present invention, it is preferred that the first threshold value represents a change of the parameter after a start of the reaction and the second threshold value represents a change of the parameter after the first threshold value. Also, in the assay of the present invention, it is preferred that the first threshold value is set within 0.1 to 10% of a maximum change of the parameter of the enzyme reaction and the second threshold value is set within 0.3 to 50% of the maximum change of the parameter of the enzyme reaction, respectively.

The parameter of the enzyme reaction is preferably absorbance, turbidity, transmitted light intensity, fluorescence polarization, or scattered light intensity. These parameters change depending on an amount of a pigment formed from a chromogenic synthetic peptide substrate by the enzyme reaction, on an amount of melanin, or on a degree of gelation. The substance that is involved in the enzyme reaction is preferably endotoxin, (1→3)-β-D-glucan, or peptidoglycan. The enzyme reaction is preferably a Limulus reaction or a phenol oxidase precursor cascade reaction.

In a preferred embodiment of the present invention, the substance involved in the enzyme reaction is endotoxin or (1→3)-β-D-glucan, the first threshold value is set within 0.5 to 7% of a maximum change of the parameter of the enzyme reaction, the second threshold value is set within 1 to 10% of the maximum change of the parameter of the enzyme reaction, the enzyme reaction is the Limulus reaction, and a pigment which is produced from a chromogenic synthetic peptide substate by a clotting enzyme is measured in terms of absorbance as the parameter of the enzyme reaction, or formation of coagulin by a clotting enzyme is measured in terms of absorbance or turbidity as the parameter of the enzyme reaction.

According to the present invention, it is possible to measure rapidly and accurately with greatly reduced errors the enzyme reaction which has a change in the rate of reaction.

DETAILED DESCRIPTION OF THE INVENTION

The invention will be described below in more detail with reference to its preferred embodiments.

The assay of the present invention is a method for measuring an enzyme reaction, to determine a substance involved in the enzyme reaction. Specifically, it is a method for measuring a time course of a parameter of the enzyme reaction which changes as the enzyme reaction produces the reaction product, to determine the amount of the substance involved in the enzyme reaction, which is characterized in that the method comprises setting a first threshold value and a second threshold value of the parameter of the enzyme reaction, starting time measurement from a point at which the value of the parameter reaches to the first threshold value, to measure a time required for the parameter of the enzyme reaction to change from the first threshold value to the second threshold value, and correlating the time measured to the amount of the substance involved in the enzyme reaction.

The term "enzyme reaction" as used herein includes those reactions in which a plurality of enzymes are involved. The reactions in which a plurality of enzymes are involved include the entirety of and individual steps of the sequential reactions (cascade reactions) in which a plurality of enzymes are involved. Examples thereof to which the assay of the present invention is preferably applied include: (1) Limulus reaction, that is, an enzyme reaction which involves a blood coagulation cascade mechanism of horseshoe crabs; and (2) phenol oxidase precursor cascade reaction, that is, an enzyme reaction which involves a cascade mechanism for melanization of body fluid of insects. For more detail about the Limulus reaction and the Limulus test utilizing it and the phenol oxidase precursor cascade reaction and the SLP reagent utilizing it, refer to "Tosekieki endotokishin ga yoku wakaru hon (Book for understanding endotoxin in dialysing fluid)", Shingo Takezawa ed., Tokyo Igakusha Ltd. (1995), pp. 31–41, 137–143.

The substance involved in the above-mentioned enzyme reaction means any substance which affects the rate of the enzyme reaction or the amount of the reaction product of the enzyme reaction. Examples include any enzyme and its substrate which play the principal part in the enzyme reaction and any substance to trigger activation of an enzyme precursor. The substrate to trigger activation of the enzyme precursor is exemplified by endotoxin, (1→3)-β-D-glucan, and peptidoglycan, which activate an enzyme precursor to trigger a series of reactions in the Limulus reaction or the phenol oxidase precursor cascade reaction. The assay of the present invention can be used to determine the amount of the above-mentioned substances. Specifically, for example, it can be applied to determination involving the enzyme reaction such as determination of the amount of endotoxin or (1→3)-β-D-glucan by means of the Limulus reaction; determination of the amount of peptidoglycan or (1→3)-β-D-glucan by means of the phenol oxidase precursor cascade reaction; or determination of the amount of blood coagulation factor or fibrinolysis factor, by means of blood coagulation/fibrinolysis system.

The parameter of the enzyme reaction is defined as a value which accurately reflects the change of amount of the above-mentioned enzyme reaction products and changes according to the amount of the enzyme reaction product. Such parameter of the enzyme reaction is exemplified by absorbance, turbidity, transmitted light intensity, fluorescence polarization, scattered light intensity of the reaction solution, and moreover, pH, conductivity, specific ionization, specific resistance, etc. which are changed as a result of the enzyme reaction. Any values may be preferably used so long as they can be converted into electric or magnetic signals, or can be amplified. Absorbance, turbidity, and transmitted light intensity are preferable parameters to be used to determine the substances involved in the Limulus reaction and the phenol oxidase precursor cascade reaction mentioned above, although they are not limitative.

For example, to determine the amount of endotoxin or (1→3)-β-D-glucan by using the Limulus reaction, the clotting enzyme activity is determined by measuring the pigment (determined in terms of absorbance) which is produced from the known chromogenic synthetic peptide substrate, or by measuring the gelation (determined in terms of absorbance or turbidity), i.e., the formation of coagulin gel caused via the action of clotting enzyme on the coagulogen contained in, or separately added to Limulus reagent.

Examples of the chromogenic synthetic peptide substrate include chromogenic synthetic peptide substrates for factors in Limulus reagent, whose peptide has an amino acid sequence such as Val-Pro-Arg, Leu-Gly-Arg, or Ile-Glu-Ala-Arg (SEQ ID No: 1) or D-hexahydrotyrosyl-Gly-Arg. The amino group at N-terminal of the peptide may be protected by an amino-protecting residue [e.g., Boc, Fmoc, Z, Tos, methoxycarbonyl], and the carboxyl group of arginine at C-terminal of the peptide is combined through amide bonding with a chromogenic residue [e.g., residues of p-nitroaniline, p-(N,N-diethylamino)aniline, p-(N-ethyl-N-β-hydroxylethyl)aniline]. The chromogenic synthetic peptide substrates produce pigments [e.g., p-nitroaniline, p-(N,N-diethylamino)aniline, p-(N-ethyl-N-β-hydroxylethyl)aniline] by the Limulus reaction.

As an example for determining the amount of (1→3)-β-D-glucan or peptidoglycan by using the phenol oxidase precursor cascade reaction including pro-phenoloxidase-activating enzyme, phenoloxidase, and the like, the enzyme activity is determined by measuring the produced melanin (determined in terms of absorbance) from L-3,4-dihydroxyphenylalanine as the final product of the phenol oxidase precursor cascade.

According to the assay of the present invention, two threshold values are set with respect to the parameter. The first threshold value of the above-mentioned threshold values generally denotes the extent to which the parameter has changed from the parameter of the enzyme reaction (initial value) after the start of the reaction. It is set within a range of preferably 0.1 to 10%, more preferably 0.5 to 7% of the maximum change of the parameter of the enzyme reaction (The maximum change is abbreviated as Δmax for convenience). The second threshold value generally denotes the extent to which the parameter has changed from the first threshold value. It is set within a range of preferably 0.3 to 50% of Δmax, more preferably 0.5 to 25% of Δmax, still more preferably 1 to 10% of Δmax.

The maximum change of the parameter can be calculated by a preliminary test which employs as a standard reference material the substance of known concentration involved in the enzyme reaction. In the case where the chromogenic synthetic peptide substrate is used, it can be calculated previously the respective threshold values from the amount of the chromogenic synthetic substrate because the maximum change of the parameter of the enzyme reaction depends on the amount of the chromogenic synthetic peptide substrate to be used. The thus calculated maximum change makes it possible to establish the threshold values in advance.

In the case where rapidity is not required, there may be an alternative procedure as follows. All of the parameter values are measured throughout the enzyme reaction and the maximum change is calculated from them after the reaction is completed. Then, the first and second threshold values are established according to this maximum change. Finally, the time required for the parameter to change from the first threshold value to the second threshold value is calculated from the measured values.

As the methods for measuring the time required for the parameter of the enzyme reaction to change from the first threshold value to the second threshold value, there may be mentioned a method comprising continuously reading off and plotting the values of the parameter of the enzyme reaction at certain time intervals, and a method comprising assuming the values of the parameter immediately before and after reaching each threshold value as a continuous change to determine a corrected value converted by a regression formula of first order on the assumption. The latter is preferable because of higher accuracy.

The time required for the parameter of the enzyme reaction to change from the first threshold value to the second threshold value may be correlated to the amount of the substance involved in the enzyme reaction by preparing a calibration curve for the standard reference material, and using the time measured for the sample and the calibration curve.

The assay of the present invention may be carried out in the same manner as in the conventional enzyme reaction assay based on the measurement of the parameter of the enzyme reaction except that the time required for the parameter to change from the first threshold value to the second threshold value is measured. That is, reagents to be used and reaction conditions may be the same as in the conventional one.

A specific example of the determination of endotoxin is given below. A sample or a reference material solution is mixed with all or part of the Limulus reagent containing factors B and C, serine protease precursor, and a chromogenic synthetic peptide substrate [e.g., Boc-Leu-Gly-Arg-CONH-pNA] as a substrate for clotting enzyme which are each involved in the Limulus reaction. The resulting mixture undergoes reaction at a prescribed temperature. The time required for the absorbance or the transmitted light intensity of the reaction solution to undergo the change specified in the present invention is measured. The result of measurement is compared with the calibration curve prepared by measuring the time required in the case of the reference material, to determine the amount of endotoxin in the sample.

The determination of the amount of (1→3)-β-D-glucan may be accomplished by using the Limulus reagent containing factor G, serine protease precursor, and a chromogenic synthetic peptide substrate [e.g., Boc-Leu-Gly-Arg-CONH-pNA] as a substrate for clotting enzyme.

The reagent used to determine the amount of peptidoglycan includes the following. For example, (i) a reagent such as SLP reagent or the body fluid of insects which contains the phenol oxidase precursor cascade to react with at least peptidoglycan, (ii) the reagent or the body fluid of insects mentioned above to which a substance such as (1→3)-β-D-glucan-binding protein, anti-(1→3)-β-D-glucan antibody, (1→3)-β-D-glucan hydrolase, aprotinin, and alkylglucoside, which substantially inhibits the phenol oxidase precursor cascade reaction by (1→3)-β-D-glucan, is incorporated. Any of these reagents is mixed with a sample or a solution of reference peptidoglycan, and reacted at a prescribed temperature. The time required for the absorbance or the transmitted light intensity of the reaction solution to change as much as prescribed in the present invention is measured. The result of measurement is compared with the calibration curve prepared by measuring the time for the reference peptidoglycan, to determine the amount of peptidoglycan. The measurement of absorbance can be accomplished by any known method used to measure the absorbance of the melanin formed by the phenol oxidase precursor cascade reaction.

In the case where (1→3)-β-D-glucan is determined by using the phenol oxidase precursor cascade reaction, it is possible to use (1) the reagent or the body fluid of insects which contains the phenol oxidase precursor cascade to be triggered by (1→3)-β-D-glucan or (2) the reagent or the like in which the reagent or the body fluid of insects mentioned above (1) is mixed with anti-peptidoglycan-recognizing protein antibody, a strong alkali (e.g., sodium hydroxide, lithium hydroxide, and potassium hydroxide), lysozyme, protease, or anti-peptidoglycan antibody. It is possible to determine, using these reagents, the amount of (1→3)-β-D-glucan in samples as in the case of the above-mentioned peptidoglycan.

The assay of the present invention may be practiced by using any apparatus at least having the following means.
(1) Means of inputting and storing the threshold values.
(2) Means of measuring the parameter of the enzyme reaction, and inputting and storing the measured values.
(3) Means of measuring the time required for the parameter of the enzyme reaction to change from the first threshold value to the second threshold value, and storing the measured values.
(4) Means of displaying the time required for the change.

The means of inputting the threshold values, mentioned in (1) above may be a keyboard, a touch panel, or a ten-key board, which is not specifically limited. The means of measuring the parameter of the enzyme reaction, mentioned in (2) above is not specifically limited so long as it is capable of measuring the parameter of the enzyme reaction in the assay of the present invention. It should preferably be an absorption photometer or spectrophotometer capable of measuring the absorbance or the transmitted light intensity which is the preferred embodiment of the parameter of the enzyme reaction. The means mentioned in (4) above may be an electric light display panel or a liquid-crystal display panel. The storing means of value and time, mentioned in (1) to (3) above include electronic storage media (e.g., RAM and memory card), magnetic storage media (e.g., optical disk, hard disk, and floppy disk), and paper media (e.g., punch card), which are not limitative.

The apparatus having the above-mentioned means may have, according to the necessity, such components as a display for the values stored in respective means (electric light display panel or liquid-crystal panel), a thermostatic chamber, a timer, or a printer. It may also have an electronic control system to handle the assay of the present invention with a number of samples simultaneously by using reaction vessels such as 96-well multiplate. Further, it may have additional components including means of calculating the regression formula that represents the relation between the concentration of the reference material and the time required for the reference material to change and calculating the concentration of the substance to be measured in the sample from the calculated regression formula and the time required for the sample to change; and means of displaying the concentration of the substance to be measured in the sample.

The above-mentioned means may be arranged integrally or separately to constitute the desired apparatus.

EXAMPLES

The invention will be described in more detail with reference to the following examples. It is to be understood that the examples may be modified variously without departing from the object of the invention and that the examples are not to be construed to limit the scope of the invention.

Example 1

A standard material according to the Japanese pharmacopoeia of endotoxin derived from *E. coli* UKT-B, was properly diluted with injectable distilled water to prepare five endotoxin solutions varying in concentration (10 EU/ml, 2.5 EU/ml, 0.625 EU/ml, 0.156 EU/ml, and 0.039 EU/ml). These standard solutions and the sample tested by rabbit pyrogen test according to the Japanese Pharmacopoeia were pipetted (50 μl each) into the wells of a 96-well microplate ("Toxipet plate 96F" from Seikagaku Corp.). Further, to each well was added 50 μl of the endotoxin-specific Limulus reagent for colorimetry ("Endospecy" from Seikagaku Corp.). The microplate was then set on the measuring apparatus and kept at 37° C. for 30 minutes for reactions to proceed. The change in absorbance at 405 nm (492 nm for control) was monitored at intervals of 15 seconds (kinetic colorimetry). From the monitored values were calculated the respective measurement values by the following two methods.

(i) The Assay of the Present Invention (Delta T Assay)

The first threshold value is set to 0.005 and the second threshold value is set to 0.015 (The first threshold value of 0.005 corresponds to 0.7% of the maximum change of 0.7 (calculated from the amount of the chromogenic synthetic peptide substrate contained in the endotoxin-specific Limlus reagent for colorimetry), and the second threshold value of 0.015 corresponds to 1.9% of the maximum change of 0.7 mentioned above.). The time required for the parameter of the enzyme reaction to change from the first threshold value at which the absorbance is 0.005 to the second threshold value at which the absorbance is 0.020 which in the amount of change from the first threshold value is 0.015, was measured.

(ii) Colorimetric Reaction Time Assay

The time required for the parameter to reach the preset absorbance of 0.015 from the start of the reaction was measured.

The logarithms of the values measured in these modes was plotted against the logarithms of endotoxin concentrations to give a calibration curve. From this calibration curve was calculated automatically the concentration of endotoxin in three samples tested by the rabbit pyrogen test according to the Japanese pharmacopoeia. Three rabbits (weighing 1.8 to 2 kg) in good healthy and nutritional conditions were used in the test. After injection, the body temperature in the rectum was measured three times at intervals of one hour. The result was regarded as positive if 2 or 3 rabbits experienced the temperature rise of 0.6° C. or more (positive at 0.5 EU/ml and above). The results are shown in Table 1. It is apparent from Table 1 that the conventional method gives a lower activity than the rabbit pyrogen test, which the calorimetric reaction time assay which one of the conventional reaction time assays (delta OD-time assays) in which the time required for three samples varying in the endotoxin concentration to reach a certain threshold value is analyzed. If injections are tested for safety by the colorimetric reaction time assay in place of the rabbit pyrogen test, a false negative result (<0.5 EU/ml) would be obtained as in the sample No. 2. On the other hand, the assay of the present invention is free from such discrepancy, and it gives the same pyrogenic activity as in the rabbit pyrogen test which is an endotoxin assay other than the Limlus test.

TABLE 1

Correlation between the amount of endotoxin determined
by the assay of the present invention and the calorimetric
reaction time assay and the result of the rabbit pyrogen test

| | | Analysis mode | | |
|---|---|---|---|---|
| | Sample | Assay of the present invention | Colorimetric reaction time assay | Rabbit pyrogen test |
| | | Time measured (min) | | |
| Standard solution (EU/ml) | 0.039 | 4.6 | 12.4 | − |
| | 0.156 | 1.8 | 8.6 | − |
| | 0.625 | 0.7 | 6.2 | + |
| | 2.500 | 0.3 | 3.5 | + |
| | 10.000 | 0.1 | 2.0 | + |
| | Coefficient of correlation | 0.999 | 0.992 | |
| | Concentration of endotoxin in samples (EU/ml) | | | |
| Sample | No. 1 | 0.08 | 0.03 | − |
| | No. 2 | 0.66 | 0.34* | + |
| | No. 3 | 5.76 | 2.80 | + |

*False-negative data

Example 2

The endotoxin solutions and samples used in Example 1 were pipetted (50 μl each) into the wells of Toxipet plate 96F. To each well was added 50 μl of Limulus HS Test Wako (from Wako Pure Chemical Industries, Ltd.). The Toxipet plate was then set on the measuring apparatus and kept at 37° C. for 60 minutes for reactions to proceed. The change in absorbance at 405 nm was monitored at intervals of 15 seconds (kinetic turbidimetry). From the monitored values, the time was culculated in the same manner as in Example 1, by setting the first threshold value to 0.010 and the second threshold value to 0.020, starting the measurement when the turbidity reached the first threshold value, and measuring the time (min.) required for the turbidity to change from the first threshold value to the second threshold value ((i) the assay of the present invention). Also, the endotoxin solutions and samples were pipetted (100 μl each) into test tubes, and to each test tube was added 100 μl of Limulus HS Test Wako, and after mixing, the test tubes were placed in a turbidity time analyzer ("Toxinometer ET301," from Wako Pure Chemical Industries, Ltd.) which is capable of measuring a time course of transmitted light intensity and measuring the time (min.) required for the turbidity to reach a certain level, and then reactions were proceeded at 37° C. for 60 minutes and measured ((ii) turbidimetric time assay).

The results are shown in Table 2. It is apparent from Table 2 that when applied to the kinetic turbidimetry, the assay of the present invention produces the same results (with same strengths) as in pyrogenic activity for all the samples as in the case where it is applied to the kinetic calorimetric method in Example 1. By contrast, the conventional turbidimetric time assay gives a lower activity than pyrogenic activity, resulting in discrepancy, as in the colorimetric reaction time assay in Example 1. A false negative result (<0.5 EU/ml) was observed for pyrogenic activity as in sample No. 2.

TABLE 2

Correlation between the amount of endotoxin determined
by the assay of the present invention and the turbidimetric
time assay and the rabbit pyrogen test

| | | Analysis mode | | |
|---|---|---|---|---|
| | Sample | Assay of the present invention | Turbi-dimetric time assay | Rabbit pyrogen test |
| | | Time measured (min) | | |
| Standard solution (EU/ml) | 0.039 | 12.5 | 37.2 | − |
| | 0.156 | 3.5 | 25.0 | − |
| | 0.625 | 1.3 | 14.6 | + |
| | 2.500 | 0.5 | 8.5 | + |
| | 10.000 | 0.2 | 3.0 | + |
| | Coefficient of correlation | 0.998 | 0.982 | |
| | Concentration of endotoxin in samples (EU/ml) | | | |
| Sample | No. 1 | 0.08 | 0.02 | − |
| | No. 2 | 0.66 | 0.30* | + |
| | No. 3 | 5.76 | 2.51 | + |

*False-negative data

Example 3

Solutions of varied concentrations prepared from a standard material according to the Japanese pharmacopoeia of endotoxin derived from *E. coli* UKT-B and a standard material according to the United States pharmacopoeia of endotoxin derived from *E. coli* 0113 were pipetted (50 μl each) into the well of the Toxipet plate 96F. To each well was added 50 μl of Endospecy. The plate was set on the measuring apparatus. Measurements were carried out in the same manner as in Example 1. From the measured values, the time was culculated according to the assay of the present invention and the conventional calorimetric reaction time assay, as in Example 1. These logarithms were plotted against the logarithms of endotoxin concentrations, and the regression formulae of first order were calculated. Thus obtained four calibration curves were compared with one another. The results are shown in Table 3.

It is apparent from Table 3 that the conventional calorimetric reaction time assay, which is designed to measure the time required for the parameter to reach a present value, gives two regression curves which greatly differ in slope, whereas the assay of the present invention gives two regression curves which are not significantly different. In other words, according to the assay of the present invention, it is possible to accurately determine the amount of endotoxin in samples regardless of its kind by using a calibration curve prepared from a standard reference material of endotoxin of one kind.

TABLE 3

Comparison of calibration curves obtained by different methods from standard reference material of endotoxin of two kinds

| Endotoxin standard solution (EU/ml) | Analysis mode | | | |
|---|---|---|---|---|
| | Colorimetric reaction time assay (min) | | Assay of the present invention (min) | |
| | UKT-B | O113 | UKT-B | O113 |
| 0.039 | 12.4 | 4.8 | 4.6 | 4.5 |
| 0.156 | 8.6 | 1.1 | 1.1 | 1.0 |
| 0.625 | 6.2 | 0.7 | 0.6 | 0.6 |
| 2.500 | 3.5 | 0.3 | 0.3 | 0.3 |
| 10.000 | 2.0 | 0.2 | 0.2 | 0.2 |
| Regression formula of first order | y = −0.328x + 0.534 | y = −0.552x − 0.561 | y = −0.546x − 0.598 | y = −0.536x − 0.616 |

Note:
UKT-B: Reference endotoxin derived from *E. coli* UKT-B, according to the Japanese Pharmacopoeia
O113: Reference endotoxin derived from *E. coli* O113, according to the United States Pharmacopoeia

---

---

What is claimed is:

1. A method for measuring an enzyme reaction to determine an amount of a substance involved in the enzyme reaction wherein said substance is endotoxin, (1→3)-β-D-glucan, or peptidoglycan, and said enzyme reaction is a Limulus reaction or a phenol oxidase precursor cascade reaction, which method comprises the steps of:

preselecting a parameter of the enzyme reaction, said parameter being indicative of a time course of the enzyme reaction, starting the enzyme reaction, measuring a time required for the parameter of the enzyme reaction to change from a first threshold value to a second threshold value, said first threshold value being set within 0.1 to 10% of a maximum change in the parameter of the enzyme reaction, and correlating the measured time to an amount of the substance involved in the enzyme reaction.

2. The method according to claim 1, wherein the second threshold value represents a change of the parameter after the first threshold value.

3. The method according to claim 1, wherein the first threshold value is set within 0.1 to 10% of a maximum change of the parameter of the enzyme reaction and the second threshold value is set within 0.3 to 50% of the maximum change of the parameter of the enzyme reaction.

4. The method according to claim 1, wherein the parameter of the enzyme reaction is absorbance, turbidity, transmitted light intensity, fluorescence polarization, or scattered light intensity.

5. The method according to claim 1, wherein the substance involved in the enzyme reaction is endotoxin or (1→3)-β-D-glucan, the first threshold value is set within 0.5 to 7% of a maximum change of the parameter of the enzyme reaction, the second threshold value is set within 1 to 10% of the maximum change of the parameter of the enzyme reaction, the enzyme reaction is a Limulus reaction, and a pigment which is produced from a chromogenic synthetic peptide substrate by a clotting enzyme is measured in terms of absorbance as the parameter of the enzyme reaction.

6. The method according to claim 1, wherein the substance involved in the enzyme reaction is endotoxin or (1→3)-β-D-glucan, the first threshold value is set within 0.5 to 7% of a maximum change of the parameter of the enzyme reaction, the second threshold value is set within 1 to 10% of the maximum change of the parameter of the enzyme reaction, the enzyme reaction is a Limulus reaction, and formation of coagulin by a clotting enzyme is measured in terms of absorbance or turbidity as the parameter of the enzyme reaction.

\* \* \* \* \*

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: chromogenic synthetic peptide substrate

<400> SEQUENCE: 1

Ile Glu Ala Arg